(12) United States Patent
Modha et al.

(10) Patent No.: US 7,329,442 B2
(45) Date of Patent: Feb. 12, 2008

(54) ELASTOMERIC GLOVES HAVING IMPROVED DONNABILITY

(75) Inventors: Shanti Modha, Alpharetta, GA (US); Mary Elizabeth Kister, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/223,583

(22) Filed: Aug. 19, 2002

(65) Prior Publication Data

US 2003/0118837 A1 Jun. 26, 2003

Related U.S. Application Data

(63) Continuation-in-part of application No. 10/036,743, filed on Dec. 21, 2001.

(51) Int. Cl.
*A41D 19/00* (2006.01)
*B32B 27/00* (2006.01)
*B32B 27/40* (2006.01)
*B29D 22/00* (2006.01)
*B29D 23/00* (2006.01)

(52) U.S. Cl. ............... 428/35.7; 428/423.1; 428/423.9; 428/425.5; 428/447; 428/36.8; 2/161.7; 2/168; 2/167; 2/159; 2/161.8

(58) Field of Classification Search ............... 428/36.8, 428/35.7, 423.1, 423.9, 493, 425.5, 424.2, 428/447; 2/161.7, 168, 159, 167, 161.8; 524/589–591
See application file for complete search history.

(56) References Cited

U.S. PATENT DOCUMENTS

| | | | |
|---|---|---|---|
| 2,755,194 A | 7/1956 | Volkmann et al. | |
| 3,382,138 A | 5/1968 | Barth | |
| 3,411,982 A | 11/1968 | Kavalir et al. | |
| 3,426,099 A * | 2/1969 | Freifeld et al. | 525/127 |
| 3,485,787 A | 12/1969 | Haefele et al. | |
| 3,740,262 A | 6/1973 | Agostinelli | |
| 3,762,978 A | 10/1973 | Holmes et al. | |
| 3,808,287 A | 4/1974 | Thomas | |
| 3,813,695 A | 6/1974 | Podell, Jr. et al. | |
| 3,830,767 A | 8/1974 | Condon | |
| 3,872,515 A | 3/1975 | Miner et al. | |

(Continued)

FOREIGN PATENT DOCUMENTS

EP 189773 8/1986

(Continued)

OTHER PUBLICATIONS

Article—Product Profile—NiSil Silicone Technology—High Profile Silicone Primer (Clear) CF1-135.

(Continued)

*Primary Examiner*—Rena Dye
*Assistant Examiner*—Catherine A. Simone
(74) *Attorney, Agent, or Firm*—Dority & Manning, P.A.

(57) ABSTRACT

An elastomeric glove that contains a donning layer containing waterborne polyurethane and a lubricant formed from a silicone emulsion is provided. It has discovered that the application of a waterborne polyurethane donning layer and silicone emulsion lubricant to the inner surface of the glove may provide both damp and dry donnability to the resulting elastomeric glove.

36 Claims, 2 Drawing Sheets

U.S. PATENT DOCUMENTS

| | | |
|---|---|---|
| 3,928,271 A | 12/1975 | Matsuda et al. |
| 3,933,702 A | 1/1976 | Caimi et al. |
| 3,971,745 A | 7/1976 | Carlson et al. |
| 3,975,294 A | 8/1976 | Dumoulin |
| 3,991,026 A | 11/1976 | Matsuda et al. |
| 3,992,221 A | 11/1976 | Homsy et al. |
| 4,006,116 A | 2/1977 | Dominguez |
| 4,016,122 A | 4/1977 | Matsuda et al. |
| 4,016,123 A | 4/1977 | Matsuda et al. |
| 4,027,060 A | 5/1977 | Esemplare et al. |
| 4,039,629 A | 8/1977 | Himes et al. |
| 4,041,103 A | 8/1977 | Davison et al. |
| 4,052,331 A | 10/1977 | Dumoulin |
| 4,061,709 A | 12/1977 | Miller et al. |
| 4,070,713 A | 1/1978 | Stockum |
| 4,082,862 A | 4/1978 | Esemplare et al. |
| 4,143,109 A | 3/1979 | Stockum |
| 4,146,499 A | 3/1979 | Rosano |
| 4,156,066 A | 5/1979 | Gould |
| 4,156,067 A | 5/1979 | Gould |
| 4,167,507 A | 9/1979 | Haaf |
| 4,248,751 A | 2/1981 | Willing |
| 4,255,296 A | 3/1981 | Ogawa et al. |
| 4,260,530 A | 4/1981 | Reischl et al. |
| 4,302,852 A | 12/1981 | Joung |
| 4,304,008 A | 12/1981 | Joung |
| 4,309,557 A | 1/1982 | Compton et al. |
| 4,310,928 A | 1/1982 | Joung |
| 4,329,312 A | 5/1982 | Ganz |
| 4,359,558 A | 11/1982 | Gould et al. |
| 4,367,302 A | 1/1983 | Le Roy et al. |
| 4,386,179 A | 5/1983 | Sterling |
| 4,394,473 A | 7/1983 | Winter et al. |
| 4,434,126 A | 2/1984 | McGary, Jr. et al. |
| 4,448,922 A | 5/1984 | McCartney |
| 4,451,635 A | 5/1984 | Gould et al. |
| 4,463,156 A | 7/1984 | McGary, Jr. et al. |
| 4,472,291 A | 9/1984 | Rosano |
| 4,481,323 A | 11/1984 | Sterling |
| 4,482,571 A | 11/1984 | Abraham |
| 4,499,154 A | 2/1985 | James et al. |
| 4,511,354 A | 4/1985 | Sterling |
| 4,548,844 A | 10/1985 | Podell et al. |
| 4,576,156 A | 3/1986 | Dyck et al. |
| 4,597,108 A | 7/1986 | Momose |
| 4,613,640 A | 9/1986 | Deisler et al. |
| 4,620,878 A | 11/1986 | Gee |
| 4,660,228 A | 4/1987 | Ogawa et al. |
| 4,670,330 A | 6/1987 | Ishiwata |
| 4,670,500 A | 6/1987 | Gupta |
| 4,684,490 A | 8/1987 | Taller et al. |
| 4,755,337 A | 7/1988 | Takahashi et al. |
| 4,777,224 A | 10/1988 | Gorzynski et al. |
| 4,783,857 A | 11/1988 | Suzuki et al. |
| 4,789,720 A | 12/1988 | Teffenhart |
| 4,810,543 A | 3/1989 | Gould et al. |
| 4,851,266 A | 7/1989 | Momose et al. |
| 4,857,565 A | 8/1989 | Henning et al. |
| 4,882,378 A | 11/1989 | Himes |
| 4,888,829 A | 12/1989 | Kleinerman et al. |
| 4,902,558 A | 2/1990 | Henriksen |
| 4,917,850 A | 4/1990 | Gray |
| 4,920,172 A | 4/1990 | Daoud |
| 4,947,487 A | 8/1990 | Saffer et al. |
| 4,957,970 A | 9/1990 | Holsapple et al. |
| 4,983,662 A | 1/1991 | Overbeek et al. |
| 5,011,409 A | 4/1991 | Gray |
| 5,014,361 A | 5/1991 | Gray |
| 5,014,362 A | 5/1991 | Tillotson et al. |
| 5,020,162 A | 6/1991 | Kersten et al. |
| 5,026,607 A | 6/1991 | Kiezulas |
| 5,039,750 A | 8/1991 | Miller et al. |
| 5,068,138 A | 11/1991 | Mitchell et al. |
| 5,069,965 A | 12/1991 | Esemplare |
| 5,079,300 A | 1/1992 | Dubrow et al. |
| 5,084,514 A | 1/1992 | Szczechura et al. |
| 5,088,125 A | 2/1992 | Ansell et al. |
| 5,089,205 A | 2/1992 | Huang et al. |
| 5,112,900 A | 5/1992 | Buddenhagen et al. |
| 5,120,816 A | 6/1992 | Gould et al. |
| 5,132,129 A | 7/1992 | Potter et al. |
| 5,138,719 A | 8/1992 | Orlianges et al. |
| 5,146,628 A | 9/1992 | Herrmann et al. |
| 5,164,231 A | 11/1992 | Davis |
| 5,169,571 A | 12/1992 | Buckley |
| 5,171,809 A | 12/1992 | Hilty et al. |
| 5,195,537 A | 3/1993 | Tillotson |
| 5,196,263 A | 3/1993 | Melby et al. |
| 5,202,368 A | 4/1993 | Davies et al. |
| 5,214,095 A | 5/1993 | Lavoie |
| 5,227,242 A | 7/1993 | Walter et al. |
| 5,228,947 A | 7/1993 | Churchland |
| 5,272,012 A | 12/1993 | Opolski |
| 5,272,771 A | 12/1993 | Ansell et al. |
| 5,277,976 A | 1/1994 | Hogle et al. |
| 5,284,607 A | 2/1994 | Chen |
| 5,302,440 A | 4/1994 | Davis |
| 5,306,558 A | 4/1994 | Takahashi et al. |
| 5,310,517 A | 5/1994 | Dams et al. |
| 5,332,612 A | 7/1994 | Payet et al. |
| 5,338,169 A | 8/1994 | Buckley |
| 5,343,586 A | 9/1994 | Vosbikian |
| 5,370,900 A | 12/1994 | Chen |
| 5,391,343 A | 2/1995 | Dreibelbis et al. |
| 5,395,666 A | 3/1995 | Brindle |
| 5,399,400 A | 3/1995 | Nile et al. |
| 5,405,666 A | 4/1995 | Brindle |
| 5,407,715 A | 4/1995 | Buddenhagen et al. |
| 5,409,739 A | 4/1995 | Liu |
| 5,429,686 A | 7/1995 | Chiu et al. |
| 5,438,709 A | 8/1995 | Green et al. |
| 5,444,121 A | 8/1995 | Grennes et al. |
| 5,458,588 A | 10/1995 | Amdur et al. |
| 5,458,936 A | 10/1995 | Miller et al. |
| 5,534,350 A | 7/1996 | Liou |
| 5,536,921 A | 7/1996 | Hedrick et al. |
| 5,545,451 A | 8/1996 | Haung et al. |
| 5,548,862 A | 8/1996 | Curtis |
| 5,554,673 A | 9/1996 | Shah |
| 5,570,475 A | 11/1996 | Nile et al. |
| 5,571,219 A | 11/1996 | Gorton |
| 5,571,567 A | 11/1996 | Shah |
| 5,573,637 A | 11/1996 | Ampulski et al. |
| 5,576,382 A | 11/1996 | Seneker et al. |
| 5,595,628 A | 1/1997 | Gordon et al. |
| 5,601,870 A | 2/1997 | Haung et al. |
| 5,607,980 A | 3/1997 | McAtee et al. |
| 5,609,727 A | 3/1997 | Hansen et al. |
| 5,612,083 A | 3/1997 | Haung et al. |
| 5,614,293 A | 3/1997 | Krzysik et al. |
| 5,620,773 A | 4/1997 | Nash |
| 5,625,900 A | 5/1997 | Hayes |
| 5,643,588 A | 7/1997 | Roe et al. |
| 5,644,798 A | 7/1997 | Shah |
| 5,649,326 A | 7/1997 | Richard, Jr. et al. |
| 5,650,218 A | 7/1997 | Krzysik et al. |
| 5,650,225 A | 7/1997 | Dutta et al. |
| 5,661,208 A | 8/1997 | Estes |
| RE35,616 E | 9/1997 | Tillotson et al. |
| 5,663,213 A | 9/1997 | Jones et al. |
| 5,674,818 A | 10/1997 | Garcia Puig et al. |
| 5,691,069 A | 11/1997 | Lee |
| 5,700,585 A | 12/1997 | Lee |
| 5,706,522 A | 1/1998 | Ballarino et al. |

| | | |
|---|---|---|
| 5,712,346 A | 1/1998 | Lee |
| 5,716,692 A | 2/1998 | Warner et al. |
| 5,728,063 A | 3/1998 | Preissman et al. |
| 5,728,065 A | 3/1998 | Follmer et al. |
| 5,728,340 A | 3/1998 | Dreibelbis et al. |
| 5,736,251 A | 4/1998 | Pinchuk |
| 5,742,943 A | 4/1998 | Chen |
| 5,759,173 A | 6/1998 | Preissman et al. |
| 5,789,354 A | 8/1998 | Mikami et al. |
| 5,792,531 A | 8/1998 | Littleton et al. |
| 5,804,318 A | 9/1998 | Pinchuk et al. |
| 5,807,921 A | 9/1998 | Hill et al. |
| 5,833,915 A | 11/1998 | Shah |
| 5,849,000 A | 12/1998 | Anjur et al. |
| 5,851,683 A | 12/1998 | Plamthottam et al. |
| 5,864,913 A | 2/1999 | Robertson et al. |
| 5,881,386 A | 3/1999 | Horwege et al. |
| 5,881,387 A | 3/1999 | Merovitz et al. |
| 5,886,089 A | 3/1999 | Knowlton |
| 5,900,452 A | 5/1999 | Plamthottam |
| 5,906,823 A | 5/1999 | Mixon |
| 5,913,871 A | 6/1999 | Werneth et al. |
| 5,916,203 A | 6/1999 | Brandon et al. |
| 5,916,678 A | 6/1999 | Jackson et al. |
| 5,920,942 A | 7/1999 | Footer |
| 5,931,774 A | 8/1999 | Williams et al. |
| 5,948,710 A | 9/1999 | Pomplun et al. |
| 5,958,178 A | 9/1999 | Bartsch et al. |
| 5,958,275 A | 9/1999 | Joines et al. |
| 5,958,558 A | 9/1999 | Giesfeldt et al. |
| 5,962,620 A | 10/1999 | Reich et al. |
| 5,965,276 A | 10/1999 | Shlenker et al. |
| 5,974,589 A | 11/1999 | Pugh et al. |
| 5,977,223 A | 11/1999 | Ryan et al. |
| 5,985,392 A | 11/1999 | Hert et al. |
| 5,985,955 A | 11/1999 | Bechara et al. |
| 5,987,685 A | 11/1999 | Lambert |
| 5,991,926 A | 11/1999 | Lakusiewicz |
| 5,993,923 A | 11/1999 | Lee |
| 5,993,972 A | 11/1999 | Reich et al. |
| 5,997,969 A | 12/1999 | Gardon |
| 5,998,540 A | 12/1999 | Lipkin et al. |
| 6,000,089 A | 12/1999 | Renken |
| 6,001,300 A | 12/1999 | Buckley |
| 6,016,570 A | 1/2000 | Vande Pol et al. |
| 6,017,997 A | 1/2000 | Snow et al. |
| 6,019,922 A | 2/2000 | Hassan et al. |
| 6,020,580 A | 2/2000 | Lewis et al. |
| 6,021,524 A | 2/2000 | Wu et al. |
| 6,044,494 A | 4/2000 | Kang |
| 6,044,513 A | 4/2000 | Penn |
| 6,048,932 A | 4/2000 | Okada et al. |
| 6,051,320 A | 4/2000 | Noecker et al. |
| 6,082,915 A | 7/2000 | Kimmel |
| 6,120,477 A | 9/2000 | Campbell et al. |
| 6,136,039 A | 10/2000 | Kristinsson et al. |
| 6,143,416 A | 11/2000 | Brindle et al. |
| 6,160,151 A | 12/2000 | Compton et al. |
| 6,243,938 B1 | 6/2001 | Lubrecht |
| 6,264,791 B1 | 7/2001 | Sun et al. |
| 6,284,856 B1 | 9/2001 | Lee |
| 6,288,109 B1 | 9/2001 | Chatterjee et al. |
| 6,288,159 B1 | 9/2001 | Plamthottam |
| 6,306,514 B1 | 10/2001 | Weikel et al. |
| 6,316,541 B1 | 11/2001 | Gee |
| 6,322,665 B1 | 11/2001 | Sun et al. |
| 6,345,394 B1 | 2/2002 | Nakamura et al. |
| 6,346,583 B1 | 2/2002 | Kilgour et al. |
| 6,347,408 B1 | 2/2002 | Yeh |
| 6,378,137 B1 | 4/2002 | Hassan et al. |
| 6,389,602 B1 | 5/2002 | Alsaffar |
| 6,391,963 B1 | 5/2002 | Nishiyama |
| 6,414,083 B2 | 7/2002 | Plamthottam |
| 2002/0015812 A1 | 2/2002 | Littleton et al. |
| 2004/0253459 A1 | 12/2004 | Triebes et al. |

FOREIGN PATENT DOCUMENTS

| | | |
|---|---|---|
| EP | 0681912 A2 | 11/1995 |
| EP | 0681912 A3 | 11/1995 |
| EP | 0543657 B1 | 1/1996 |
| EP | 0609387 B1 | 7/1999 |
| EP | 1036810 A2 * | 9/2000 |
| EP | 0757059 B1 | 12/2002 |
| GB | 912753 | 12/1962 |
| WO | WO 8100345 | 2/1981 |
| WO | WO 8904647 A1 | 6/1989 |
| WO | WO 9308236 | 4/1993 |
| WO | WO 9324068 A1 | 12/1993 |
| WO | WO 9625278 A1 | 8/1996 |
| WO | WO 9922686 | 5/1999 |
| WO | WO 0035978 A1 | 6/2000 |
| WO | WO 0065083 A2 | 11/2000 |
| WO | WO 0065083 A3 | 11/2000 |
| WO | WO 0065084 | 11/2000 |
| WO | WO 0065096 | 11/2000 |
| WO | WO 0065347 | 11/2000 |
| WO | WO 0065348 | 11/2000 |
| WO | WO 0141700 A2 | 6/2001 |
| WO | WO 0142250 A3 | 6/2001 |
| WO | WO 0178620 A1 | 10/2001 |
| WO | WO 0241815 A2 | 5/2002 |

OTHER PUBLICATIONS

Article—Product Profile Silicone Technology—High Profile Silicone Primer (Clear) CF2-135.

Article—Product Profile Silicone Technology—Addition Cure High Tear Silicone Despersion—MED 10-6640.

Article—Product Profile Silicone Technology—Addition Cure High Tear Silicone Despersion—MED 10-6400.

Article—Product Profile Silicone Technology—Addition Cure High Tear Silicone Despersion—MED 10-6600.

Encyclopedia of Polymer Science and Engineering, vol. 13: pp. 277,292,293; Published by Wiley & Sons Inc., 1988.

Technical Bulletin of Byosylk & Active Bond from Delta Polymer Systems SDN. BHD., 7 pages, Jun. 2, 1993.

Abstract of DE 19618006, Nov. 6, 1997.

Abstract of JP 59-150,184, Aug. 28, 1984.

U.S. Appl. No. 10/161,546, filed Jun. 3, 2002, Modha, et al., Elastomeric Gloves Having Improved Gripping Characteristics.

* cited by examiner

ELASTOMERIC GLOVES HAVING IMPROVED DONNABILITY

RELATED APPLICATIONS

The present application is a continuation-in-part of U.S. application Ser. No. 10/036,743, filed on Dec. 21, 2001 which is now pending.

BACKGROUND OF THE INVENTION

Elastomeric gloves, such as surgical and examination gloves, have traditionally been made of natural or synthetic elastomers to provide a combination of good elasticity and strength. Due to their tight fit over the hand, however, elastomeric gloves are often difficult to don. To overcome this problem, powdered lubricants were traditionally applied to the inside surface of the glove to reduce friction between the skin and the elastomer. As an example, epichlorohydrin-treated maize crosslinked starch was a common powder applied to the inside of elastomeric gloves during manufacture to permit them to be more readily slipped onto the hand of the user.

Unfortunately, the use of powdered lubricants has drawbacks in specific situations, such as the case of surgical gloves. Specifically, if some of the powder escapes from the inside of the glove into the surgical environment, as for example if the glove is torn during the surgery, the powder may enter the surgical wound and cause further complications for the patient. The powder may also carry infectious agents and/or cause allergenic reactions in the patient.

As a result, various other techniques were developed to aid in the donnability of elastomeric gloves. For example, the surface of natural rubber latex gloves has been chlorinated to reduce friction between the wearer-contacting surface and a user's skin when donned. Moreover, other techniques have also been developed to enhance the lubricity of a glove's inner surface. One such technique is described in U.S. Pat. No. 5,792,531 to Littleton, et al. For instance, in one example, Littleton, et al. describes forming a donning layer on an S-EB-S glove from an S-I-S mid-block unsaturated block copolymer, chlorinating the resulting glove in a washing machine, and then applying a lubricant to the wearer-contacting surface of the glove that contains cetyl pyridinium chloride and a silicone emulsion (DC 365 from Dow Corning). Another technique is described in U.S. Pat. No. 5,008,125 to Ansell, et al. and U.S. Pat. No. 5,272,771 to Ansell, et al. For example, the Ansell, et al. patents describe a glove modified by an ionic polyurethane that allows donning without the use of powders and renders the glove hypoallergenic. In addition, still another technique is described in U.S. Pat. No. 6,347,408 to Yeh. For instance, Yeh describes a glove having an inner coating formed of a crosslinked polyurethane that has been impregnated with a silicone, which is said to provide an improvement over gloves coated on their inner surface with a non-crosslinked polyurethane.

Although conventional techniques, such as described above, have resulted in some improvement in the donning characteristics of elastomeric gloves, a need still exists for an elastomeric glove that is able to achieve excellent damp and dry donning characteristics.

SUMMARY OF THE INVENTION

In accordance with one embodiment of the present invention, an elastomeric glove having wet and dry donnability is disclosed. The glove comprises a substrate body including a layer made of an elastomeric material, the substrate body having an inside surface and an outside surface. In some embodiments, for example, the elastomeric material of the substrate body is selected from the group consisting of styrene-ethylene-butylene-styrene block copolymers, styrene-isoprene-styrene block copolymers, styrene-butadiene-styrene block copolymers, styrene-isoprene block copolymers, styrene-butadiene block copolymers, natural rubber latex, nitrile rubbers, isoprene rubbers, chloroprene rubbers, polyvinyl chlorides, silicone rubbers, and combinations thereof.

The glove also includes a donning layer overlying the inside surface of the substrate body, the donning layer being formed from a water-soluble polyurethane. In one embodiment, the water-soluble polyurethane is formed by reacting a polyurethane prepolymer with a chain extender. The prepolymer may be formed, for instance, by reacting a polyisocyanate (e.g., aliphatic polyisocyante) with a polyol (e.g., polyester polyol). A water-solublizing compound may be further reacted with the polyol and polyisocyanate to form the polyurethane prepolymer.

In addition to a substrate body and a donning layer, the elastomeric glove also includes a lubricant that coats the donning layer. The lubricant is formed from a silicone emulsion. In some embodiments, the silicone emulsion contains a polysiloxane having at least one functional group selected from the group consisting of amino, carboxyl, hydroxyl, ether, polyether, aldehyde, ketone, amide, ester, thiol groups, and combinations thereof.

In accordance with another embodiment of the present invention, a method for enhancing the wet and dry donnability of an elastomeric glove is disclosed. The method comprises:

providing a hand-shaped former;

dipping the hand-shaped former into a bath containing an elastomeric polymer to form a substrate body of the glove;

dipping the hand-shaped former into an aqueous polyurethane solution to form a donning layer of the glove;

applying a silicone emulsion to form a lubricant of the glove.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
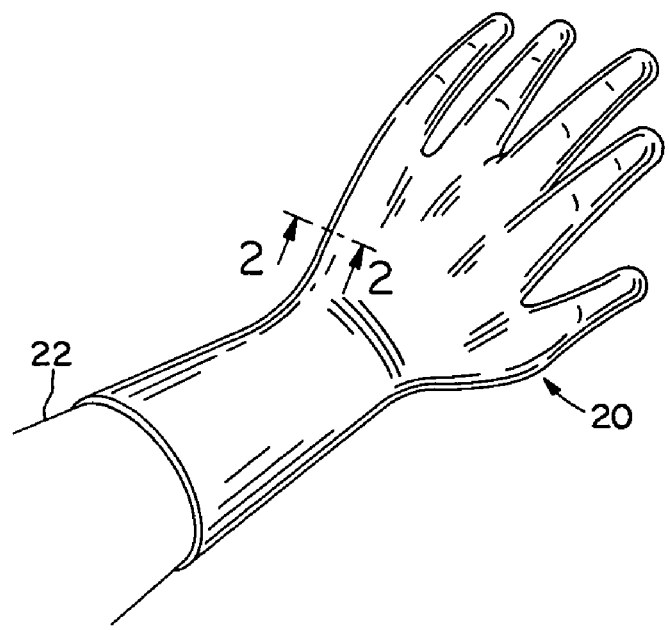
FIG. 1 is a perspective view of one embodiment of an elastomeric glove made according to the invention.

Repeat use of reference characters in the present specification and drawings is intended to represent the same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to an elastomeric article, such as a condom or glove, that contains a polyurethane donning layer and a silicone emulsion lubricant. For example, in one embodiment, the glove contains a natural rubber latex substrate body, a donning layer that contains a water-soluble polyurethane, and a lubricant formed from a silicone emulsion. It has been discovered that the application of a polyurethane donning layer and silicone emulsion lubricant to the inner surface of the glove may provide both damp and dry donnability to the resulting elastomeric glove.

Figure 2:
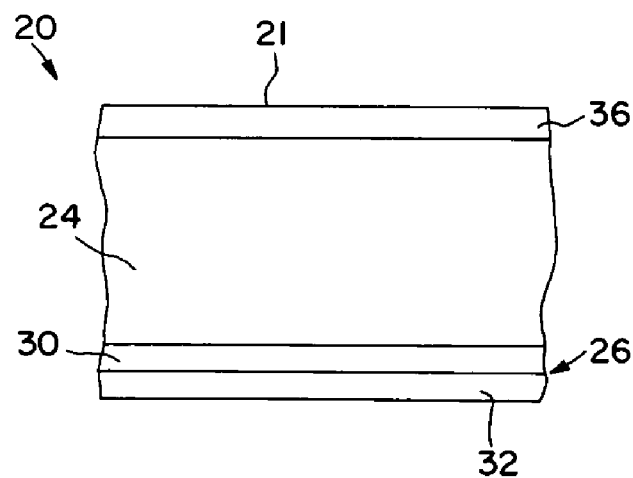
FIG. 2 is a cross-sectional view of the glove illustrated in FIG. 1 taken along a line 2-2.

Referring to FIGS. 1-2, for example, one embodiment of an elastomeric glove 20 is illustrated that may be placed on the hand of a user 22. The glove 20 includes a substrate body 24 having the basic shape of the glove. The substrate body 24 may generally be formed from any of a variety of natural and/or synthetic elastomeric materials known in the art. For instance, some examples of suitable elastomeric materials include, but are not limited to, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, natural rubber latex, nitrile rubbers, isoprene rubbers, chloroprene rubbers, polyvinyl chlorides, silicone rubbers, and combinations thereof. Other suitable elastomeric materials that may be used to form the substrate body 24 may be described in U.S. Pat. No. 5,112,900 to Buddenhagen, et al.; U.S. Pat. No. 5,407,715 to Buddenhagen, et al.; U.S. Pat. No. 5,900,452 to Plamthottam; U.S. Pat. No. 6,288,159 to Plamthottam; and U.S. Pat. No. 6,306,514 to Weikel, et al., which are incorporated herein in their entirety by reference thereto for all purposes.

In one embodiment, the substrate body 24 is formed from natural rubber latex. To form the substrate body 24 from natural latex, a former is initially dipped into a coagulant bath that facilitates later stripping of the glove from the former. The coagulant bath may include calcium carbonate and/or calcium nitrate. Thereafter, the coagulant-coated former is dried and subsequently dipped into one or more latex baths. The resulting latex layer(s) are then typically leached in water to extract a large percentage of the water-soluble impurities in the latex and coagulant. The coated former is then dried to cure (i.e., crosslink) the rubber. It should be understood that the conditions, process, and materials used in forming natural rubber gloves are well known in the art, and are not critical to the practice of the present invention.

Regardless of the particular material used to form the substrate body 24, the glove 20 also includes a coating 26 that contacts the body of the user 22 during use. In this embodiment, the coating 26 includes a donning layer 30 overlying and contacting the substrate body 24 and a lubricant 32 overlying and contacting the donning layer 30.

The donning layer 30 may contain any of a variety of different elastomeric polymers that are capable of facilitating donning of the glove. For example, in one particular embodiment, the donning layer 30 contains a water-soluble polyurethane. Various water-soluble polyurethanes that may be used in the present invention are described in U.S. Pat. No. 6,017,997 to Snow, et al., which is incorporated herein in its entirety by reference thereto for all purposes. For instance, in one embodiment, the polyurethane polymer may be synthesized by reacting a polyisocyanate with an active hydrogen containing, high molecular weight product, such as a long-chain polyol or a long-chain polyamide, and a water-solubilizing compound having water-solubilizing groups to form an isocyanate terminal prepolymer. The prepolymer is subsequently neutralized with a tertiary amine and dispersed in water. The dispersed prepolymer is then chain-extended using a functional primary and/or secondary amine having at least two active hydrogens.

Any of a variety of organic polyisocyanates may generally be utilized in the present invention to form the polyurethane of the donning layer 30. For instance, some examples of suitable isocyanates include, but are not limited to, aliphatic, cycloaliphatic, araliphatic, and aromatic polyisocyanates, used alone or in mixtures of two or more. Specific examples of aliphatic polyisocyanates include alpha, omega-alkylene diisocyanates having from 5 to 20 carbon atoms, such as hexamethylene 1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, and mixtures thereof. Specific examples of suitable cycloalipahtic polyisocyanates include dicyclohexlymethane diisocyanate, isophorone diisocyanate, 1,4-cyclohexane diisocyanate, 1,4-cyclohexane bis(methylene isocyanate), 1,3-bis(isocyanatomethyl) cyclohexane, and mixtures thereof. Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate and mixtures thereof. Further, specific examples of suitable aromatic diisocyanates include methane-bis (4-phenyl isocyanate), toluene diisocyanate and their isomers.

As mentioned above, the isocyanate may be reacted with a polyol to form the polyurethane prepolymer. A polyol is generally any high molecular weight product having an active hydrogen component that may be reacted and includes materials having an average of about two or more hydroxyl groups per molecule. Long-chain polyols may be used that include higher polymeric polyols, such as polyester polyols and polyether polyols, as well as other acceptable "polyol" reactants, which have an active hydrogen component such as polyester polyols, polyhydroxy polyester amides, hydroxyl containing polycaprolactones, hydroxy-containing acrylic interpolymers, hydroxy-containing epoxies, and hydrophobic polyalkylene ether polyols.

The polyester polyols are esterification products prepared by the reaction of organic polycarboxylic acids or their anhydrides with a stoichiometric excess of a polyol. Examples of suitable polyols include, but are not limited to, polyglycol adipates, polyethylene terephthalate polyols, polycaprolactone polyols, orthophthalic polyols, and sulfonated polyols, etc. The polycarboxylic acids and polyols are typically aliphatic or aromatic dibasic acids and diols. The diols used in making the polyester include alkylene glycols, e.g., ethylene glycol, butylene glycol, neopentyl glycol and other glycols such as bisphenol A, cyclohexane diol, cyclohexane dimethanol, caprolactone diol, hydroxyalkylated bisphenols, and polyether glycols. Suitable carboxylic acids include dicarboxylic acids and tricarboxylic acids, e.g., maleic acid, succinic acid, glutaric acid, adipic acid, pimelic acid, azelaic acid, sebacic acid, chlorendic acid, 1,2,4-butane-tricarboxylic acid, phthalic acid, terephthalic acid, and the isomers of phthalic acid.

Besides long-chain polyols, a long-chain amine may also be used to form the polyurethane prepolymer. Suitable amines include, but are not limited to, Jeffamine® D-2000 and D-4000, which are amine-terminated polypropylene glycols, differing only by molecular weight, and which are available from Huntsman Chemical Company. It is also recognized that other difunctional active hydrogen containing materials in a suitable molecular weight range (averaging from about 2500 to about 5500 amu), may be suitable.

To enhance the water-solubility of the polyurethane polymer, a water-solubilizing compound bearing a group that is water-soluble or may be made water-soluble is incorporated into the polymer chain. One particularly preferred water-solubilizing compound is 2,2-bis(hydroxymethyl) propionic acid, which is also known as dimethylol propanoic acid (DMPA). Other suitable water-solubilizing compounds include, but are not limited to, tartaric acid, dimethylol butanoic acid (DMBA), glycollic acid, thioglycollic acid, lactic acid, malic acid, dihydroxy malic acid, dihydroxy tartaric acid, and 2,6-dihydroxy benzoic acid.

Water-solubilizing groups may be incorporated in the prepolymer in an inactive form and activated by a salt-forming compound, such as a tertiary amine. The water-solubilizing groups are typically hydrophilic or ionic groups that assist solubility or dispersability of the polymer in water and enhance the stability of polymer dispersions. The water-solubilizing compound is generally present in an amount of from about 2 wt.% to about 4 wt.% of the total prepolymer.

The formation of the isocyanate terminal prepolymer may be achieved without the use of a catalyst. However, a catalyst may be used in some embodiments. Examples of suitable catalysts include stannous octoate, dibutyl tin dilaurate and tertiary amine compounds, such as triethyl amine and bis(dimethylaminoethyl) ether, morpholine compounds such as β, β-dimorpholinodiethyl ether, bismuth carboxylates, zincbismuth carboxylates, iron (III) chloride, potassium octoate, potassium acetate, and DABCO® (bicycloamine). When utilized, the amount of catalyst is typically from about 10 to about 40 parts per million of the isocyanate terminal prepolymer.

A prepolymer diluent may be used to lower the viscosity of the copolymer dispersion. One particular diluent that may be used is N-methyl pyrrolidone (NMP), which does not contain reactive groups and thus will not generally interfere with the reaction. Typically, the diluent is utilized in an amount of from 0% to about 10% by weight of the polyurethane dispersion. In some embodiments, however, the copolymer dispersion is prepared in the absence of a diluent. In this case, the prepolymer may be made so the resultant viscosity is minimized. In neat (no solvent) and solution polymers, viscosity is largely determined by the molecular weight of the polymer. To minimize the molecular weight of a finished prepolymer, an NCO/OH ratio of 2/1 may be used. In this way the diol portions are essentially endcapped by the diisocyanate species, leaving an isocyanate terminal prepolymer of relatively low viscosity. As the NCO/OH ratio of a prepolymer is reduced, the resultant viscosity typically increases. It should be understood, however, that diluent-free materials may be made at NCO/OH ratios below or greater than 2/1 if desired.

Neutralization of the prepolymer having dependent carboxyl groups with the tertiary amine converts the carboxyl groups to carboxylate anions, thus having a solubilizing effect. Suitable tertiary amines that may be used to neutralize the polymer include, but are not limited to, primary or secondary amines, triethyl amine, dimethyl ethanol amine, and N-methyl morpholine.

As noted above, a chain extender may also be utilized in forming the polyurethane polymer. The nature of the chain extender may vary widely. For example, in some embodiments, bifunctional compounds, such as diols, may be used as the chain extender. Some examples of diol chain extenders include, but are not limited to, ethane-1,2-diol, propane-1,2-diol, propane-1,3-diol, butane-1,4-diol, hexane-1,6-diol, 2,3-dimethylbutane-2,3-diol, 2,5-dimethylhexane-2,5-diol. In addition, organic and/or inorganic amines may also be used. Examples of such chain extenders include, but are not limited to, ethylene diamine, propylene diamine, butylene diamine, hexamethylene diamine, cyclohexylene diamine, phenylene diamine, meta-xylylene diamine, tolylene diamine, xylylene diamine, 3,3-dichlorobenzidene, 4,4-methylene-bis (2-chloroaniline), and 3,3-dichloro-4,4-diamino diphenylmethane, propane-1,3-diamine, propane-1,2-diamine, butane-1,4-diamine, 2-methylpentane-1,5-diamine, hexane-1,6-diamine, diethylene triamine, ethanolamine, aminoethyl ethanolamine, 1-aminopropan-2-ol, 3-aminopropan-1-ol, 2-aminopropan-1-ol, 2-aminobutan-1-ol, and 4-aminobutan-1-ol. Hydrazine, an inorganic amine, may be used to finish off any excess extension necessary. Other suitable inorganic amines may include ammonia, substituted hydrazines, and hydrazine reaction products.

The solids content of the water-soluble polyurethane used to form the donning layer 30 may generally be varied to achieve the desired donning properties. For example, the water-soluble polyurethane used to form the donning layer 30 may have a solids content of from about 1 weight % to about 10 weight %. In another embodiment, the water-soluble polyurethane used to form the donning layer 30 may have a solids content of from about 1 weight % to about 3 weight %. In still another embodiment, the water-soluble polyurethane used to form the donning layer 30 may have a solids content of from about 5 weight % to about 8 weight %. To lower the solids content of a commercially available water-soluble polyurethane, for example, one or more solvents (e.g., water, alcohols, etc.) may be utilized. By varying the solids content of water-soluble polyurethane, the presence of polyurethane in the glove may be controlled. For example, to form a glove with a higher degree of donning properties, the polyurethane used in such layer may have a relatively high solids content so that a greater percentage of the polyurethane is incorporated into the layer during the forming process. The thickness of the donning layer may also vary. For example, the thickness may range from about 0.5 micrometers to about 20 micrometers. In another embodiment, the thickness may range from about 1 micrometer to about 10 micrometers. In still another embodiment, the thickness may range from about 1 micrometer to about 5 micrometers.

A lubricant 32 that contains a silicone emulsion also coats the donning layer 30 to aid in donning the article when the user's body is either wet or dry. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups.

Generally, any silicone capable of enhancing the donning characteristics of the glove 20 may be used in the silicone emulsion. In some embodiments, polydimethylsiloxane and/ or modified polysiloxanes may be used as the silicone component of the emulsion in the present invention. For instance, some suitable modified polysiloxanes that may be used in the present invention include, but are not limited to, phenyl-modified polysiloxanes, vinyl-modified polysiloxanes, methyl-modified polysiloxanes, fluoro-modified polysiloxanes, alkyl-modified polysiloxanes, alkoxy-modified polysiloxanes, amino-modified polysiloxanes, and combinations thereof.

Some suitable phenyl-modified polysiloxanes include, but are not limited to, dimethyldiphenylpolysiloxane copolymers; dimethyl, methylphenylpolysiloxane copolymers; polymethylphenylsiloxane; and methylphenyl, dimethylsiloxane copolymers. Phenyl modified polysiloxanes that have a relatively low phenyl content (less than about 50 mole %) may be particularly effective in the present invention. For example, the phenyl-modified polysiloxane may be a diphenyl-modified silicone, such as a diphenylsiloxane-modified dimethylpolysiloxane. In some embodiments, the phenyl-modified polysiloxanes contain phenyl units in an amount from about 0.5 mole % to about 50 mole %, in some embodiments in an amount less than about 25 mole %, and in some embodiments, in an amount less than about 15 mole %. In one particular embodiment, a diphenylsiloxane-modified dimethylpolysiloxane may be used that contains diphenylsiloxane units in an amount less than about 5 mole %, and particularly in an amount less than about 2 mole %. The diphenylsiloxane-modified dimethylpolysiloxane may be synthesized by reacting diphenylsiloxane with dimethylsiloxane.

As indicated above, fluoro-modified polysiloxanes may also be used in the present invention. For instance, one suitable fluoro-modified polysiloxane that may be used is a trifluoropropyl modified polysiloxane, such as a trifluoropropylsiloxane modified dimethylpolysiloxane. A trifluoropropylsiloxane modified dimethylpolysiloxane may be synthesized by reacting methyl, 3,3,3 trifluoropropylsiloxane with dimethylsiloxane.

The fluoro-modified silicones may contain from about 5 mole % to about 95 mole % of fluoro groups, such as trifluoropropylsiloxane units. In another embodiment, the fluoro-modified silicones may contain from about 40 mole % to about 60 mole % of fluoro groups. In one particular embodiment, a trifluoropropylsiloxane-modified dimethylpolysiloxane may be used that contains 50 mole % trifluoropropylsiloxane units.

Besides the above-mentioned modified polysiloxanes, other modified polysiloxanes may also be utilized in the present invention. For instance, some suitable vinyl-modified polysiloxanes include, but are not limited to, vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; and vinylphenylmethyl terminated polydimethylsiloxanes. Further, some methyl-modified polysiloxanes that may be used include, but are not limited to, dimethylhydro terminated polydimethylsiloxanes; methylhydro, dimethylpolysiloxane copolymers; methylhydro terminated methyloctyl siloxane copolymers; and methylhydro, phenylmethyl siloxane copolymers. In addition, some examples of amino-modified polysiloxanes include, but are not limited to, polymethyl(3-aminopropyl)-siloxane and polymethyl[3-(2-aminoethyl)aminopropyl]-siloxane.

The particular polysiloxanes described above are meant to include hetero- or co-polymers formed from polymerization or copolymerization of dimethylsiloxane cyclics and diphenylsiloxane cyclics or trifluoropropylsiloxane cyclics with appropriate endcapping units. Thus, for example, the terms "diphenyl modified dimethylpolysiloxanes" and "copoloymers of diphenylpolysiloxane and dimethylpolysiloxane" may be used interchangeably. Moreover, other examples of suitable polysiloxanes are believed to be described in U.S. Pat. No. 5,742,943 to Chen and U.S. Pat. No. 6,306,514 to Weikel, et al., which are incorporated herein in their entirety by reference thereto for all purposes.

Besides containing a silicone, the lubricant 32 may also contain one or more surfactants. Nonionic, anionic, cationic, and amphoteric surfactants may all be suitable for use in the present invention. For example, in some embodiments, it may be desired to utilize one or more nonionic surfactants. Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, 2,6,8-trimethyl-4-nonyloxypolyethylene oxyethanol; 2,6,8-trimethyl-4-nonyloxypolyethylene oxyethanol; alkyleneoxypolyethyleneoxyethanol; alkyleneoxypolyethyleneoxyethanol; alkyleneoxypolyethyleneoxyethanol; octylphenoxy polyethoxy ethanol; and nonylphenoxy polyethoxy ethanol, and mixtures thereof.

Additional nonionic surfactants that may be used include water soluble alcohol ethylene oxide condensates are the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable nonionic ethoxylated octyl and nonyl phenols include those having from about 7 to about 13 ethoxy units.

In addition to nonionic surfactants, the silicone emulsion may also other types of surfactants. For instance, in some embodiments, amphoteric surfactants may also be used. For instance, one class of amphoteric surfactants that may be used in the present invention are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino) propane-1-sulfonate, disodium octadecyliminodiacetate, sodium 1-carboxymethyl-2-undecylimidazole, and sodium N,N-bis (2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

In certain instances, it may also be desired to utilize one or more anionic surfactants within the silicone emulsion. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group may be straight chain (e.g., lauryl) or branched (e.g., 2-ethylhexyl). The cation of the anionic surfactant may be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride, methylbenzethonium chloride, hexadecylpyridinium chloride, benzalkonium chloride, hexadecyltrimethylammonium chloride, dodecylpyridinium chloride, the corresponding bromides, a hydroxyethylheptadecylimidazolium halide, coconut alkyldimethylammonium betaine, and coco aminopropyl betaine, may also be used in the silicone emulsion.

The amount of surfactant utilized in the silicone emulsion may generally vary depending on the relative amounts of the other components present within the emulsion. When utilized, the surfactant may be present in the emulsion in an amount from about 0.001% to about 10% by weight of the silicone emulsion used to form the lubricant 32. In another embodiment, the surfactant may be present in an amount from about 0.001% to about 5% by weight of the silicone emulsion. In still another embodiment, the surfactant may be present in an amount from about 0.01% to about 1% by weight of the silicone emulsion. For example, in one particular embodiment, a nonionic surfactant may be present in the emulsion in an amount between about 0.001% to about 5% by weight of the silicone emulsion.

The silicone emulsion may also include one or more solvents. Usually, the silicone emulsion contains at least one aqueous solvent, such as water. The silicone emulsion may also contain non-aqueous solvents that, although not required, sometimes aid in dissolving certain components of the emulsion. Examples of some suitable non-aqueous solvents include, but are not limited to, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. The amount of solvent utilized in the silicone emulsion may generally vary depending on the relative amounts of the other components present within the formulation. When utilized, the solvent is typically present in the formulation in an amount from about 20% to about 99.99% by weight of the silicone emulsion used to form the outer layer 36. In another embodiment, the solvent may be present in an amount from about 70% to about 98% by weight of the silicone emulsion.

The solids content of the lubricant 32 may generally be varied to achieve the desired donning properties. For example, the silicone emulsion used to form the lubricant 32 may have a solids content of from about 0.1 weight % to about 10 weight %. In another embodiment, the silicone emulsion may have a solids content of from about 0.25 weight % to about 5 weight %. In still another embodiment, the silicone emulsion may have a solids content of from about 0.3 weight % to about 1.0 weight %. To lower the solids content of a commercially available silicone emulsion, for example, additional amounts of solvent may be utilized. By varying the solids content of the silicone emulsion, the presence of the silicone in the glove may be controlled. For example, to form a glove with a higher degree of donning properties, the silicone emulsion used in such layer may have a relatively high solids content so that a greater percentage of the silicone is incorporated into the layer during the forming process. The thickness of the lubricant 32 may also vary. For example, the thickness may range from about 0.001 millimeters to about 0.4 millimeters. In another embodiment, the thickness may range from about 0.01 millimeters to about 0.30 millimeters. In still another embodiment, the thickness may range from about 0.01 millimeters to about 0.20 millimeters.

In one particular embodiment, the silicone emulsion is DC 365, which is a pre-emulsified silicone (35% solids content) that is commercially available from Dow Corning Corporation (Midland, Mich.) and believed to contain 40-70% water (aqueous solvent), 30-60% methyl-modified polydimethylsiloxane (silicone), 1-5% propylene glycol (non-aqueous solvent), 1-5% polyethylene glycol sorbitan monolaurate (nonionic surfactant), and 1-5% octylphenoxy polyethoxy ethanol (nonionic surfactant). In another embodiment, the silicone emulsion is SM 2140 (25% solids content), which is a pre-emulsified silicone that is commercially available from GE Silicones (Waterford, N.Y.) and believed to contain 30-60% water (aqueous solvent), 30-60% amino-modified dimethylpolysiloxane (silicone), 1-5% ethoxylated nonyl phenol (nonionic surfactant), 1-5% trimethyl-4-nonyloxypolyethyleneoxy ethanol (nonionic surfactant), and minor percentages of acetaldehyde, formaldehyde, and 1,4 dioxane. If desired, these pre-emulsified silicones may be diluted with water or other solvents prior to use in the lubricant 32.

Besides a silicone emulsion, the lubricant 32 may optionally contain other components. The lubricant 32, for example, may include a cationic (e.g., cetyl pyridinium chloride), an anionic (e.g., sodium lauryl sulfate), and/or a nonionic surfactant. Although not required, such additional components may further enhance the donning Further, besides the above-mentioned layers, the glove 20 may also contain additional layers if desired. For example, in one embodiment, the glove 20 contains an outer layer 36. Although optional, the layer 36 may be utilized to improve gripping, inhibit blocking between the layers, provide chemical resistance, and the like. For example, in one embodiment, the layer 36 includes a silicone emulsion, such as described above, that improves the gripping characteristics of the glove by inhibiting chlorination (described below).

Figure 3:
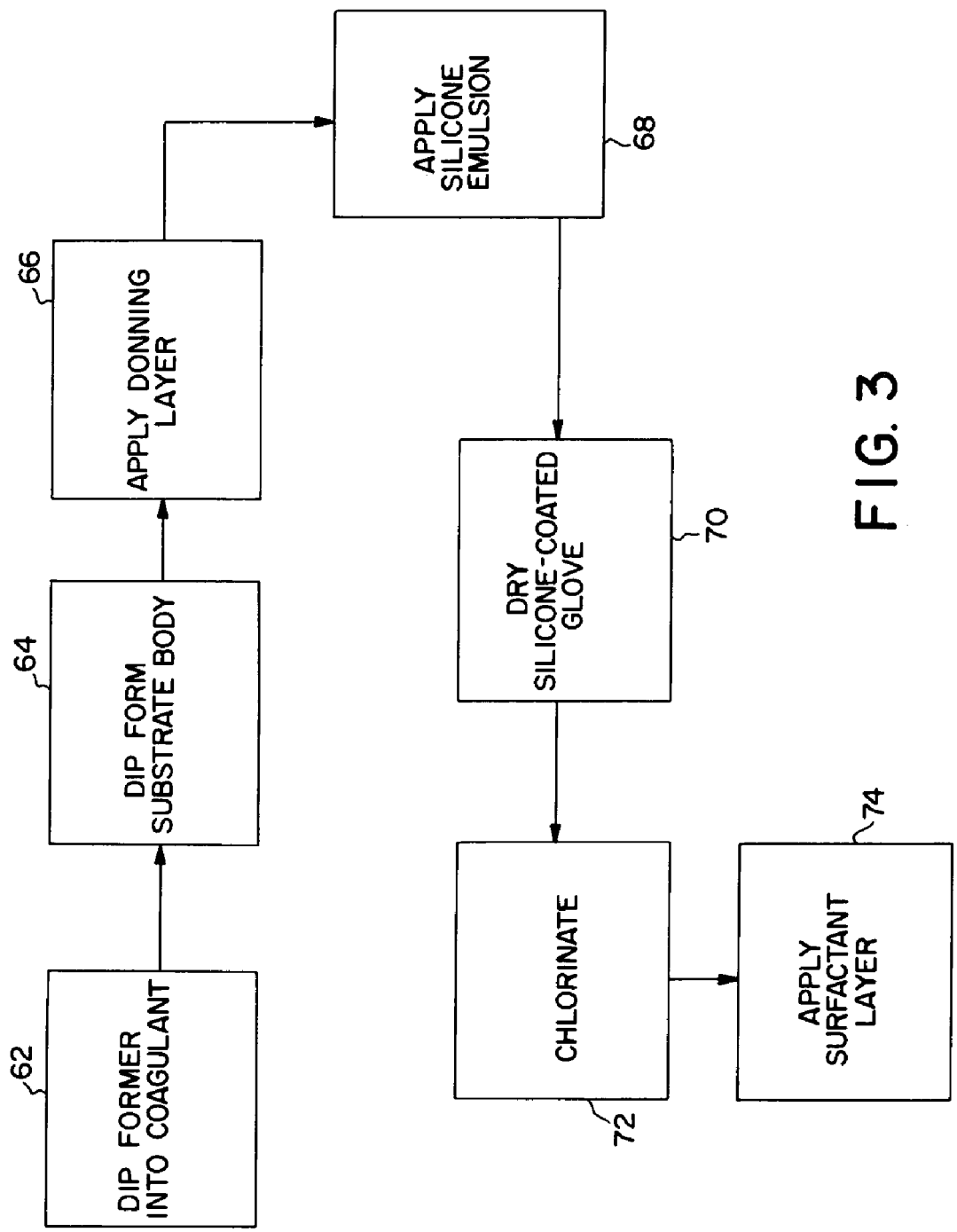
FIG. 3 is a block flow diagram illustrating one embodiment of a method for forming an elastomeric glove of the present invention.

An elastomeric article made in accordance with the present invention may generally be formed using a variety of processes known in the art. In fact, any process capable of making an elastomeric article may be utilized in the present invention. For example, elastomeric article formation techniques may utilize dipping, spraying, halogenation, drying, curing, as well as any other technique known in the art. In this regard, referring to FIG. 3, one embodiment of a method of dip-forming a glove will now be described in more detail. Although a batch process is described and shown herein, it should be understood that semi-batch and continuous processes may also be utilized in the present invention.

Initially, any well-known former, such as formers made from metals, ceramics, or plastics, is provided. The former is dried to remove water residue by conveying it through a preheated oven (not shown). The preheated former is then dipped into a bath containing a coagulant, a powder source, a surfactant, and water (illustrated as 62). The coagulant may contain calcium ions (e.g., calcium nitrate) to break the protection system of the emulsion, thereby allowing the latex to deposit on the former. The powder may be calcium carbonate powder, which later acts as a release agent. The surfactant provides good wetting to avoid forming a meniscus and trapping air between the former and deposited latex, particularly in the cuff area. As noted above, the former has been preheated in the drying step and the residual heat dries off the water leaving, for example, calcium nitrate, calcium carbonate powder, and surfactant on the surface of the former. Other suitable coagulant solutions are also described in U.S. Pat. No. 4,310,928 to Joung, which is incorporated herein in its entirety by reference thereto for all purposes.

The coated former is then dipped into a tank containing a natural rubber latex bath (illustrated as 64). The bath contains, for example, natural rubber latex, stabilizers, antioxidants, curing activators, organic accelerators, vulcanizers, and the like. The stabilizers are sometimes of the phosphate-type surfactants. The antioxidants may be the phenol type, for example, 2,2'-methylenebis (4-methyl-6-t-butylphenol). The curing activator may be zinc oxide. The organic accelerator may be dithiocarbamate. The vulcanizer may be sulfur or a sulfur-containing compound. If these materials are used, the stabilizer, antioxidant, activator, accelerator and vulcanizer may be dispersed into water to avoid crumb formation by using a ball mill. This dispersion is then mixed into the latex. The former is dipped into one or more latex baths a sufficient number of times to build up the desired thickness on the former. By way of example, the substrate body 24 may have a thickness of from about 0.004 to about 0.012 inches.

A bead roll station (not shown) may, in some embodiments, be utilized to impart a cuff to the glove. For instance, the bead roll station may contain one or more bead rolls such that the former is indexed therethrough to be provided with cuffs. The latex-coated former is then dipped into a leaching tank in which hot water is circulated to remove the water-soluble components, such as residual calcium nitrates and proteins contained in the natural latex (not shown). This leaching process may continue for about twelve minutes with the tank water being about 120° F.

The latex-coated former may then be dipped into a solution to form the donning layer 30 of the glove (illustrated as numeral 66). In one embodiment, for example, the glove is dipped into a dispersion of a water-soluble polyurethane polymer.

Thereafter, the latex-coated former is sent to a curing station where the natural rubber is vulcanized, typically in an oven, thereby heat curing the rubber (not shown). The curing station initially evaporates any remaining water in the latex coating of the former and then proceeds to the higher temperature vulcanization. The drying may occur from about 85° C. to about 95° C., with a vulcanization step occurring at temperatures from about 110° C. to about 120° C. For example, in one embodiment, the gloves may be cured in a single oven at a temperature of 115° C. for about 20 minutes. If desired, the oven may be divided into four different zones with a former being conveyed through the zones of increasing temperature. One example is an oven having four zones with the first two zones being dedicated to drying and the second two zones being primarily the vulcanization step. Each of the zones may have a slightly higher temperature, for example, the first zone at about 80° C., the second zone at about 95° C., a third zone at about 105° C., and a final zone at about 115° C. The residence time of the former within a zone in this case may be about ten minutes or so. The accelerator and vulcanizer contained in the latex coating of the former are used to cross-link the natural rubber therein. The vulcanizer forms sulfur bridges between different rubber segments and the accelerator is used to speed up sulfur bridge formation.

Upon being cured, the former may then be transferred to a stripping station (not shown). The stripping station may involve automatic or manual removal of the glove from the former. For example, in one embodiment, the glove is manually removed from the former by turning the glove inside-out as it is stripped from the former. Optionally, after being removed from the former, the glove may be rinsed in water.

Optionally, a silicone emulsion may then be applied to enhance the gripping properties of the glove. For example, in one embodiment, a silicone emulsion (e.g., DC 365) is first thoroughly mixed with water using a high shear mixer to achieve a homogeneous solution having the desired solids content. Thereafter, the resulting emulsion may then be applied to the grip surface of the glove in a variety of different ways. For instance, in one embodiment, the glove is immersed in a tumbler for a certain period of time (e.g., 1-10 minutes) during which the grip surface of the glove is rinsed with the silicone emulsion. Alternatively, the grip surface of the glove may be sprayed with the silicone emulsion using a conventional spray nozzle. Once applied with the silicone emulsion, the silicone-coated glove is then dried. For example, in some embodiments, the silicone-coated glove may be dried at a temperature of from about 20° C. to about 200° C., and in some embodiments, from about 35° C. to about 115° C.

After the drying process, the glove is then inverted and halogenated (illustrated as numeral 72). The halogenation (e.g., chlorination) may be performed in any suitable manner known to those skilled in the art. Such methods include (1) direct injection of chlorine gas into a water mixture, (2) mixing high density bleaching powder and aluminum chloride in water, (3) brine electrolysis to produce chlorinated water, and (4) acidified bleach. Examples of such methods are described in U.S. Pat. No. 3,411,982 to Kavalir; U.S. Pat. No. 3,740,262 to Agostinelli; U.S. Pat. No. 3,992,221 to Homsy, et al.; U.S. Pat. No. 4,597,108 to Momose; and U.S. Pat. No. 4,851,266 to Momose, U.S. Pat. No. 5,792,531 to Littleton, et al., which are incorporated herein in their entirety by reference thereto for all purposes. In one embodiment, for example, chlorine gas is injected into a water stream and then fed into a chlorinator (a closed vessel) containing the glove. The concentration of chlorine may be monitored and controlled to control the degree of chlorination. The chlorine concentration is typically at least about 100 ppm, in some embodiments from about 200 ppm to about 3500 ppm, and in some embodiments, from about 300 ppm to about 600 ppm, e.g., about 400 ppm. The time duration of the chlorination step may also be controlled to control the degree of chlorination and may range, for example, from about 1 to about 10 minutes, e.g., 4 minutes. Due to the silicone emulsion applied to the grip surface, chlorination will generally occur to a much greater extent on the wearer-contacting surface, i.e., the donning side of the glove, than on the grip surface of the glove.

Still within the chlorinator, the chlorinated glove may then be rinsed with tap water at about room temperature (not shown). This rinse cycle may be repeated as necessary. Once all water is removed, the glove is tumbled to drain excess water.

A lubricant solution that contains a silicone emulsion is then added into the chlorinator containing the glove that is then tumbled for about five minutes (illustrated as numeral 74). This coats the donning side with the lubricant solution to form the lubricant 32.

The coated glove is then put into a drier and dried from about 10 to 60 minutes (e.g., 40 minutes) at from about 20° C. to about 80° C. (e.g., 40° C.) to dry the donning surface (not shown). The glove is then reinverted and the grip surface is dried from about 20 to 100 minutes (e.g., 60 minutes) at from about 20° C. to about 80° C. (e.g., 40° C.).

Although various constructions and techniques for forming elastomeric articles have been described above, it should be understood that the present invention is not limited to any particular construction or technique for forming the article. For example, the layers described above may not be utilized in all instances. Additionally, other layers not specifically referred to above may be utilized in the present invention.

Thus, as discussed above, a water-soluble polyurethane donning layer and silicone emulsion lubricant may be used to enhance the donning characteristics of the glove. Specifically, it is believed that a water-soluble polyurethane dispersion may increase dry donnability, while the silicone emulsion may increase wet donnability.

The present invention may be better understood with reference to the following examples.

EXAMPLE 1

The ability to form an elastomeric glove in accordance with the present invention was demonstrated. Initially, a pre-heated, glove-shaped former was dipped into a coagulant solution that contained calcium nitrate, calcium carbonate, a surfactant, and water. The coated former was then dipped into a dip tank containing compounded, pre-vulcanized natural rubber latex. After dipping, the former was removed from the natural rubber latex dip tank and leached with water. The latex-coated former was then dipped into a solution containing 2 weight % of Hyslip 20022 and 98 weight % water to form the donning layer of the glove. Hyslip 20022 is available from Noveon, Inc. of Cleveland, Ohio and is believed to contain 26.2 wt. % of a carboxylated aliphatic polyester polyurethane, 4.8 wt. % of 1-methyl-2-pyrrolidone, and 69 wt. % water.

Thereafter, the latex-coated former was cured in an oven at a temperature of 115° C. for about 20 minutes. The glove was manually removed from the former by turning the glove inside-out as it was stripped from its corresponding former. After being removed from the former, the glove was also rinsed in deionized water. The thickness of the resulting glove was 0.24 millimeters.

After the drying process, the glove was turned inside out and placed into a chlorinator. Chlorine gas mixed with a water stream was injected into the chlorinator to chlorinate the donning surface of the glove. The chlorine concentration was 875 ppm and the pH was 1.8. The glove was immersed in the chlorine solution for 4 minutes. In this particular example, cetyl pyridinium chloride was also added to the chlorine solution at a concentration of 0.03 grams by weight of the solution. After chlorination, the glove was inverted and dried at a temperature of about 55° C. for 40 minutes.

The glove sample described above was then tested to determine the donning characteristics of the glove. Specifically, the glove was first donned on a wet hand. After donning the glove, the wearer was asked to rate the damp donnability of the wearer-contacting surface of the glove on a scale from 1 to 5, with 5 representing maximum donnability.

Specifically, the rating scale is set forth in more detail below:

Damp Donning Rating Scale

| Rating | Description | Example |
|---|---|---|
| 5 | Excellent | Easy to slide on, no adjustment required |
| 4 | Good | Gloves seats on the hand & fingers, minimal adjustment required |
| 3 | Fair | Can get the glove on the hand with reasonable fit, takes more effort and time to get on & more glove adjustment required |
| 2 | Poor | Can get most of the way on the hand, takes significant time and effort, fingers won't seat. |
| 1 | Failed | Can't get on hand |

180 samples were tested. It was determined that the average damp donning rating for the samples was 4.

EXAMPLE 2

A glove was formed with a donning layer that contained Hyslip 20022 as set forth above in Example 1. However, in this Example, after applying the polyurethane donning layer and curing the glove, the glove was removed from the former and placed in a tumbler for 5-7 minutes with a DC 365 solution (0.5 weight % solids content) to coat the gripping surface with DC 365. The glove was then inverted and chlorinated at a concentration of 1400-1800 ppm for 5-7 minutes. After being neutralized for 5-7 minutes, the glove was again placed in a tumbler for 5-7 minutes with a DC 365 solution (0.5 weight % solids content) to coat the donning surface with DC 365.

23 samples were tested. It was determined that the average damp donning rating for the samples was 3.9.

EXAMPLE 3

A glove was formed with a donning layer that contained Hyslip 20022 as set forth above in Example 1. However, in this Example, after applying the polyurethane donning layer and curing the glove, the glove was dipped into a 1% solution of cetyl pyridnium chloride. The glove was then removed from the former and placed in a tumbler for 5-7 minutes with a DC 365 solution (0.5 weight % solids content) to coat the gripping surface with DC 365. The glove was then inverted and chlorinated at a concentration of 2600-3000 ppm for 5-7 minutes. After being neutralized for 5-7 minutes, the glove was again placed in a tumbler for 5-7 minutes with a DC 365 solution (0.5 weight % solids content) to coat the donning surface with DC 365.

23 samples were tested. It was determined that the average damp donning rating for the samples was 3.7.

EXAMPLE 4

A glove was formed as set forth above in Example 3, except that after applying DC 365 to the gripping surface and inverting the glove, it was chlorinated at a concentration of 1400-1800 ppm for 5-7 minutes. 23 samples were tested. It was determined that the average damp donning rating for the samples was 3.8.

EXAMPLE 5

A glove was formed as set forth above in Example 4, except that after applying DC 365 to the gripping surface, inverting and chlorinating the glove, it was not neutralized. 23 samples were tested. It was determined that the average damp donning rating for the samples was 4.3.

EXAMPLE 6

A glove was formed as set forth above in Example 4, except that the DC 365 solution applied to the donning surface of the glove had a 1.0 weight % solids content. 23 samples were tested. It was determined that the average damp donning rating for the samples was 3.44.

EXAMPLE 7

A glove was formed as set forth above in Example 4, except that the gripping surface of the glove was not applied with a DC 365 solution. 23 samples were tested. It was determined that the average damp donning rating for the samples was 3.8.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastomeric article having wet and dry donnability, said article comprising:
   a substrate body including a layer made of an elastomeric material, said substrate body having an inside surface and an outside surface;
   a donning layer overlying the inside surface of said substrate body, said donning layer being formed from a water-soluble polyurethane, wherein said donning layer is halogenated; and
   a lubricant that coats and contacts the donning layer, said lubricant being formed from a silicone emulsion, said lubricant having a thickness from about 0.001 millimeters to about 0.4 millimeters.

2. An elastomeric article as defined in claim 1, wherein said water-soluble polyurethane is formed by reacting a polyurethane prepolymer with a chain extender.

3. An elastomeric article as defined in claim 2, wherein said prepolymer is formed by reacting a polyisocyanate with a polyol.

4. An elastomeric article as defined in claim 3, wherein said polyol is a polyester polyol.

5. An elastomeric article as defined in claim 3, wherein said polyisocyanate is an aliphatic polyisocyanate.

6. An elastomeric article as defined in claim 3, wherein a water-solubilizing compound is further reacted with said polyol and said polyisocyanate to form said polyurethane prepolymer.

7. An elastomeric article as defined in claim 2, wherein said chain extender includes an organic amine, inorganic amine, or combinations thereof.

8. An elastomeric article as defined in claim 1, wherein said water-soluble polyurethane has a solids content of from about 1 weight % to about 10 weight %.

9. An elastomeric article as defined in claim 1, wherein said donning layer has a thickness of from about 0.5 micrometers to about 20 micrometers.

10. An elastomeric article as defined in claim 1, wherein said donning layer has a thickness of from about 1 micrometer to about 5 micrometers.

11. An elastomeric article as defined in claim 1, wherein said silicone emulsion contains a polysiloxane having at least one functional group selected from the group consisting of amino, carboxyl, hydroxyl, ether, polyether, aldehyde, ketone, amide, ester, thiol groups, and combinations thereof.

12. An elastomeric article as defined in claim 1, wherein said silicone emulsion has a solids content of from about 0.1 weight % to about 10 weight %.

13. An elastomeric article as defined in claim 1, wherein said silicone emulsion has a solids content of from about 0.3 weight % to about 1.0 weight %.

14. An elastomeric article as defined in claim 1, wherein the elastomeric material of said substrate body is selected from the group consisting of styrene-ethylene-butylene-styrene block copolymers, styrene-isoprene-styrene block copolymers, styrene-butadiene-styrene block copolymers, styrene-isoprene block copolymers, styrene-butadiene block copolymers, natural rubber latex, nitrile rubbers, isoprene rubbers, chloroprene rubbers, polyvinyl chlorides, silicone rubbers, and combinations thereof.

15. An elastomeric article as defined in claim 1, wherein the elastomeric material of said substrate body is natural rubber latex.

16. An elastomeric article as defined in claim 1, wherein said lubricant further includes a surfactant.

17. An elastomeric glove as defined in claim 1.

18. An elastomeric glove having wet and dry donnability, said glove comprising:
a substrate body including a layer made of an elastomeric material, said substrate body having an inside surface and an outside surface;
a donning layer overlying the inside surface of said substrate body, said donning layer being formed from a water-soluble polyurethane that is formed by reacting a polyurethane prepolymer with a chain extender, said polyurethane prepolymer being formed by reacting an aliphatic polyisocyanate with a polyester polyol, wherein said donning layer is halogenated; and
a lubricant that coats and contacts the donning layer, said lubricant being formed from a silicone emulsion, said silicone emulsion having a solids content of from about 0.1 weight % to about 10 weight %, said lubricant having a thickness from about 0.001 millimeters to about 0.4 millimeters.

19. An elastomeric glove as defined in claim 18, wherein a water-solubilizing compound is further reacted with said polyol and said polyisocyanate to form said polyurethane prepolymer.

20. An elastomeric glove as defined in claim 18, wherein said water-soluble polyurethane has a solids content of from about 1 weight % to about 10 weight %.

21. An elastomeric glove as defined in claim 18, wherein said donning layer has a thickness of from about 0.5 micrometers to about 20 micrometers.

22. An elastomeric glove as defined in claim 18, wherein said donning layer has a thickness of from about 1 micrometer to about 5 micrometers.

23. An elastomeric glove as defined in claim 18, wherein said silicone emulsion has a solids content of from about 0.3 weight % to about 1.0 weight %.

24. An elastomeric glove as defined in claim 18, wherein the elastomeric material of said substrate body is natural rubber latex.

25. An elastomeric article as defined in claim 1, wherein said donning layer has a thickness of from about 0.5 micrometers to about 10 micrometers.

26. An elastomeric article as defined in claim 1, wherein said donning layer has a thickness of from about 1 micrometer to about 10 micrometers.

27. An elastomeric glove as defined in claim 18, wherein said donning layer has a thickness of from about 0.5 micrometers to about 10 micrometers.

28. An elastomeric glove as defined in claim 18, wherein said donning layer has a thickness of from about 1 micrometer to about 10 micrometers.

29. An elastomeric article as defined in claim 1, wherein said water-soluble polyurethane is carboxylated.

30. An elastomeric article as defined in claim 29, wherein said water-soluble polyurethane is a carboxylated aliphatic polyester polyurethane.

31. An elastomeric glove as defined in claim 18, wherein said water-soluble polyurethane is carboxylated.

32. An elastomeric glove as defined in claim 31, wherein said water-soluble polyurethane is a carboxylated aliphatic polyester polyurethane.

33. An elastomeric article as defined in claim 1, wherein said lubricant has a thickness from about 0.01 millimeters to about 0.30 millimeters.

34. An elastomeric article as defined in claim 1, wherein said lubricant has a thickness from about 0.01 millimeters to about 0.20 millimeters.

35. An elastomeric glove as defined in claim 18, wherein said lubricant has a thickness from about 0.01 millimeters to about 0.30 millimeters.

36. An elastomeric glove as defined in claim 18, wherein said lubricant has a thickness from about 0.01 millimeters to about 0.20 millimeters.

* * * * *